(12) United States Patent
Oku et al.

(10) Patent No.: US 7,994,155 B2
(45) Date of Patent: Aug. 9, 2011

(54) ACCELERATOR FOR MINERAL ABSORPTION AND USE THEREOF

(75) Inventors: Kazuyuki Oku, Okayama (JP); Michio Kubota, Okayama (JP); Shigeharu Fukuda, Okayama (JP); Toshio Miyake, Okayama (JP)

(73) Assignee: Kabushiki Kaisha Hayashibara Seibutsu Kaguku Kenkyujo, Okayama (JP)

( * ) Notice: Subject to any disclaimer, the term of this patent is extended or adjusted under 35 U.S.C. 154(b) by 625 days.

(21) Appl. No.: 11/961,899

(22) Filed: Dec. 20, 2007

(65) Prior Publication Data

US 2008/0113938 A1 May 15, 2008

Related U.S. Application Data

(62) Division of application No. 10/565,069, filed as application No. PCT/JP2004/009809 on Jul. 9, 2004, now abandoned.

(30) Foreign Application Priority Data

Jul. 18, 2003 (JP) ................................. 2003-276602

(51) Int. Cl.
 *A61K 31/702* (2006.01)
 *A61K 33/06* (2006.01)
(52) U.S. Cl. .............................. 514/61; 514/54; 424/602
(58) Field of Classification Search ........................ None
See application file for complete search history.

(56) References Cited

U.S. PATENT DOCUMENTS

| 7,192,746 B2 | 3/2007 | Kubota et al. | |
| 7,223,570 B2 * | 5/2007 | Aga et al. ......................... | 435/97 |
| 2008/0214499 A1 * | 9/2008 | Oku et al. ......................... | 514/61 |

FOREIGN PATENT DOCUMENTS

| EP | 1229112 A1 | 8/2002 |
| EP | 1284286 A1 | 2/2003 |
| EP | 1360988 A1 | 11/2003 |
| EP | 1380595 A1 | 1/2004 |
| JP | 06-205653 A | 7/1994 |
| JP | 07-033668 A | 2/1995 |
| JP | 07-067575 A | 3/1995 |
| JP | 07-069902 A | 3/1995 |
| JP | 2002-306093 A | 10/2002 |
| JP | 2002-255988 A | 11/2002 |
| WO | 01/90338 A1 | 11/2001 |
| WO | 02/10361 A1 | 2/2002 |
| WO | 02/057011 A1 | 7/2002 |
| WO | 02/072594 A1 | 9/2002 |

OTHER PUBLICATIONS

Bo, S. et al "Role of dietary magnesium in cardiovascular disease prevention . . ." Curr. Opin. Lipdol. (2008) vol. 19, pp. 50-56.*
Duffy, S. et al "Iron chelation improves endothelial function . . ." Circulation (2001) vol. 103, pp. 2799-2803.*

\* cited by examiner

*Primary Examiner* — Leigh Maier
(74) *Attorney, Agent, or Firm* — Browdy and Neimark PLLC

(57) ABSTRACT

The present invention has an object to provide an accelerator for mineral absorption and a composition containing the accelerator. The object is solved by providing an accelerator for mineral absorption comprising cyclic tetrasaccharide and/or saccharide derivatives thereof and a composition containing the accelerator.

7 Claims, No Drawings

ACCELERATOR FOR MINERAL ABSORPTION AND USE THEREOF

This is a division of co-pending parent application Ser. No. 10/565,069 filed Jan. 18, 2006, which is a national stage of under 35 U.S.C. 371 of PCT/JP04/09809, filed Jul. 9, 2004.

TECHNICAL FIELD

The present invention relates to a novel accelerator for mineral absorption and use thereof, more particularly, to a novel accelerator for mineral absorption, which contains as an effective ingredient a non-reducing saccharide composed of four glucose residues which cyclically bind each other via the α-1,3 and the α-1,6 linkages, namely, cyclo{>6)-α-D-glucopyranosyl-(1>3)-α-D-glucopyranosyl-(1>6)-α-D-glucopyranosyl-(1>3)-α-D-glucopyranosyl-(1>} (hereinafter, it is called as "cyclic tetrasaccharide"), and/or a saccharide derivative thereof, and a composition containing the accelerator for mineral absorption.

BACKGROUND ART

Minerals, for example, calcium, magnesium, phosphorus and iron, have been being analyzed to be a physiologically important nutrition for living bodies. Modern people would have to make considerable effort for continually attaining the intake of the necessary amounts of minerals everyday in their food lives. Excessive diet or aging causes breaking down hormone balances, and excessive intake of instant foods or increased frequent eating out in food life may cause a chronic mineral deficiency. Subsequently, the balance between bone-formation and bone-absorption may be broken down. Then, calcium as a main ingredient may be reduced in calcium-containing tissues such as bones and teeth. Further, bone disorders such as osteoporosis, bone fracture and backache; tooth-disorders such as dental caries and periodontosis; urinary organ disorders such as nephrolithiasis; circulatory diseases such as hypertension and ischemic heart diseases; anemia; diabetes; or reduction of homeostatic function is easily developed.

In order to solve such mineral deficiency, oily vitamins or hormone preparations such as vitamin D, calcitonin preparations, estrogen preparations, protein anabolic hormone preparations and bisphosphonate have been administered in addition to various mineral preparations. Although this method is more effective than a single administration of minerals, it is not necessarily satisfactory because of its complicated administration schedule and fear of side effect due to excessive administration of oily vitamins or hormone preparations. In addition, such mineral preparations also have a problem that they may cause the rise of blood mineral level when excessively administered.

In consideration with such situation, food business has been developing exploitation of a raw material which is tasty, safe even if administered every day, effective on promoting mineral absorption, and capable of effectively supplementing minerals in a sufficient daily amount in daily food life in a single use or in combination with meals, foods between meals, or health foods. For example, accelerators for mineral absorption, containing either xylooligosaccharide, mannooligosaccharide or lactuloseoligosaccharide as an effective ingredient, are disclosed in Japanese Patent Publication Kokai Nos. 67575/95, 306093/2002 and 205653/94, respectively. A magnesium supplement, containing magnesium and at least one member selected from the group consisting of nondigestible oligosaccharide, nondigestible sugar alcohol and dietary fiber, is disclosed in Japanese Patent Kokai No. 69902/95. An agent for strengthening bone, containing lactosucrose and calcium chondroitin sulfate, is disclosed in Japanese Patent Kokai No. 33668/95. However, some kinds of such raw materials have the following problems when added to foods and beverages; they may lower foods and beverages in flavor such as taste, smell and mouth feeling, and need a large amount to exert a satisfactory effect. While, some kinds of minerals may lower foods and beverages in preference due to its characteristic bitter taste and metal taste. To meet a variety of food life, the development of food materials having satisfactory effect on promoting mineral absorption without lowering their flavor such as taste, smell and mouth feeling, and being safe even when continually taken, has been further desired.

The present applicant disclosed a novel process for producing cyclic tetrasaccharide or a saccharide mixture containing it and its saccharide derivatives, and a composition containing them. The present applicant disclosed that these saccharides are hardly utilized by intestinal bacteria and capable of acting as a dietary fiber, in the specification of the International Publication Nos. WO 01/090338, WO 02/010361 and WO 02/072594. However, the above described patent publications, i.e. Japanese Patent Kokai No. 67575/95 through International Publication No. WO 02/072594, never disclose the fact that cyclic tetrasaccharide and/or saccharide derivatives thereof, or composition containing such saccharides have a mineral absorption-promoting action.

DISCLOSURE OF THE INVENTION

The present invention has the first object to provide an accelerator for mineral absorption, which is safely administered and is satisfactorily effective on promoting mineral absorption. The present invention has the second object to provide a composition for promoting mineral absorption, which contains the accelerator.

The present inventors have studied an accelerator for mineral absorption, which contains saccharides as effective ingredients, to attain the above objects. As a result, they revealed that cyclic tetrasaccharide and/or saccharide derivatives thereof strongly act to promote mineral absorption and to strengthen bone as a representative of strengthening calcium-containing tissues. They established a novel accelerator for mineral absorption and a composition for promoting mineral absorption, which contains the accelerator, and thus they accomplished the present invention.

BEST MODE FOR CARRYING OUT THE INVENTION

The term "composition" as referred to as in the present invention means foods, beverages, cosmetics, quasi-drugs, pharmaceuticals, feeds or pet foods. It further includes raw or intermediate materials and products produced by either processing or using them.

The term "cyclic tetrasaccharidel" as referred to as in the present invention means a non-reducing saccharide composed of four glucose residues which cyclically bind each other via the α-1,3 and the α-1,6 linkages, represented by cyclo{>6)-α-D-glucopyranosyl-(1>3)-α-D-glucopyranosyl-(1>6)-α-D-glucopyranosyl-(1>3)-α-D-glucopyranosyl-(1>}, which is disclosed in the specification of the International Publication Nos. WO 01/090338 and WO 02/010361.

The term "saccharide derivative of cyclic tetrasaccharide" as referred to as in the present invention means a saccharide where one or more of the same or different glycosyl residues are bound to cyclic tetrasaccharide; for example, a saccharide mixture having cyclic tetrasaccharide and a saccharide where one or more glucose molecules are bound to one or more hydroxyl groups of cyclic tetrasaccharide, which is obtained by allowing α-isomaltosylglucosaccharide-forming enzyme and α-isomaltosyl-transferring enzyme to act on starch. Such saccharides can be further reacted by the same or different saccharide-transferring enzymes selected from the group consisting of cyclomaltodextrin glucanotransferase, β-galactosidase, α-galactosidase, lysozyme, etc., in the presence of their substrates such as monosaccharides, oligosaccharides and/or polysaccharides according to the method disclosed by the inventors of the present invention in the specification of the International Publication No. WO 02/010361 in order to produce a saccharide having one or more of the same or different glycosyl residues selected from the group consisting of α-D-glucopyranosyl residue, β-D-galactopyranosyl residue and β-D-chitosaminyl residue at one or more hydroxyl groups of such saccharide. Furthermore, such saccharide can be transferred with one or more of the same or different glycosyl residues selected from the group consisting of α-D-glucopyranosyl residue, β-D-galactopyranosyl residue, β-D-chitosaminyl residue, etc, at the previously transferred α-D-glucopyranosyl residue, β-D-galactopyranosyl residue, or β-D-chitosaminyl residue to saccharide derivatives of cyclic tetrasaccharide.

The cyclic tetrasaccharide and saccharide derivatives thereof usable in the present invention are not specifically restricted by their origins and processes. They can be produced by fermentation method, enzymatic method, and organic synthesis. Optionally, they can contain other saccharides co-existing through the process of cyclic tetrasaccharide, such as glucose, isomaltose, maltose, oligosaccharides and dextrin. Such reaction mixtures obtainable by the above methods can be used as the cyclic tetrasaccharide and saccharide derivatives thereof in the present invention. If necessary, they are partially or highly purified by using ion-exchange resins to remove impurities. Also, a saccharide mixture, containing one or more members selected from the group consisting of a highly purified cyclic tetrasaccharide and saccharide derivatives thereof, can be used in the present invention. These cyclic tetrasaccharide and saccharide derivatives thereof can be produced from amylaceous substances or saccharides deriving therefrom by the enzymatic methods; for example, converting panose into cyclic tetrasaccharide by α-isomaltosyl-transferring enzyme, disclosed by the same applicant as the present invention in the specification of the International Publication No. WO 01/090338; or producing cyclic tetrasaccharide from starch by using α-isomaltosyl-glucosaccharide-forming enzyme and α-isomaltosyl-transferring enzyme in combination, disclosed in the specification of the International Publication No. WO 02/010361. Such cyclic tetrasaccharide and saccharide derivatives thereof can be also produced by the method disclosed by the same applicant as in the present invention in International Publication No. WO 02/072594. These methods can be used for producing cyclic tetrasaccharide and saccharide derivatives thereof in a high efficiency and a lower cost using starch as an abundant and low cost material. Therefore, the cyclic tetrasaccharide and saccharide derivatives thereof can be advantageously produced on an industrial scale. Such cyclic tetrasaccharide may be in the form of an anhydrous amorphous, anhydrous crystalline, crystalline monohydrate, or crystalline pentahydrate. Any form of cyclic tetrasaccharide can be used in the present invention. Among these, cyclic tetrasaccharide in an anhydrous crystalline, crystalline monohydrate, and anhydrous amorphous form have a satisfactory dehydrating activity. They can be used as a dehydrating agent to powderize or solidify hydrous substances by admixing with a hydrous substance such as unsaturated compounds. Therefore, cyclic tetrasaccharide in such a form can be advantageously used for producing a powdery or solid product with a high quality, which comprises cyclic tetrasaccharide as an effective ingredient.

The term "mineral" as referred to as in the present invention means a mineral required in living bodies, for example, calcium, magnesium, phosphorus, iron, manganese, sodium, potassium, copper, molybdenum, zinc, manganese, cobalt, selenium, iodine, fluorine, etc.

Mineral compounds can be contained in the accelerator of the present invention in addition to cyclic tetrasaccharide and/or saccharide derivatives thereof, and are illustrated with the above mineral compounds absorbable into living bodies, natural materials abundantly containing thereof or processed products containing thereof. Examples of calcium compounds are calcium carbonate, calcium chloride, calcium citrate, calcium gluconate, calcium glycerophosphate, calcium lactate, calcium orthophosphate, calcium hydroxide, and calcium oxide. Further, wheyey calcium, bittern, eggshell calcium, cow bone calcium, fish bone powder, coral powder, shell, or processed product thereof can also be usable.

Examples of magnesium compounds are magnesium carbonate, magnesium chloride, magnesium sulfate, magnesium acetate, magnesium gluconate, magnesium glycerophosphate, magnesium lactate, magnesium orthophosphate, magnesium hydroxide, and magnesium oxide. Further, cacao bean, almond, soy bean, peanut, bittern, rice bran, seaweed including "hijiki" (*Hiziki fusiforme*) and oarweed, and processed products thereof can also be usable because they highly contain magnesium.

Examples of potassium compounds are potassium orthophosphate, potassium citrate, potassium chloride, potassium carbonate, potassium gluconate, potassium glycerophosphate, potassium lactate, and potassium hydroxide.

Examples of sodium compounds are sodium orthophosphate, sodium citrate, sodium chloride, sodium carbonate, sodium gluconate, sodium glycerophosphate, sodium lactate, and sodium hydroxide.

Examples of iron compounds are ferrous citrate, ferrous carbonate, ammonium ferric citrate, potassium bicarbonate ferrous gluconate, ferrous lactate, ferrous sulfate, ferrous fumarate, sodium ferric phosphate (ferric biphosphate), ferric monophosphate (ferric pyrophosphate), saccharated iron oxide and elementary iron.

Examples of manganese compounds are manganese carbonate and manganese sulfate.

Examples of cobalt compounds are cobalt chloride, cobalt carbonate and cobalt sulfate.

Examples of copper compounds are cupric carbonate, cupric citrate, cupric gluconate, cupric sulfate and lysine-copper complex.

Examples of zinc compounds are zinc acetate, zinc chloride, zinc citrate, zinc gluconate, zinc lactate, zinc oxide and zinc carbonate, and zinc sulfate.

Examples of molybdenum compounds are ammonium molybdate and potassium molybdate.

Examples of selenium compounds are sodium selenate, sodium hydrogen selenite and sodium selenite.

Examples of fluorine compounds are potassium fluoride and sodium fluoride.

Examples of iodine compounds are sodium iodide, sodium iodinate, potassium iodide and potassium iodinate. Natural products or processed products abundantly containing phosphorus, iron, manganese, potassium, copper, molybdenum, iodine or fluorine are not illustrated above. However, they can be usable as proper mineral compounds for the accelerator of the present invention. According to the purpose of the accelerator of the present invention, one or more mineral compounds can be freely selected from the above mineral compounds to be incorporated in the accelerator of the present invention, optionally in combination with two more of the same or different minerals.

Other agent having the mineral absorption-promoting action can be incorporated in the accelerator of the present invention in addition to cyclic tetrasaccharide and/or saccharide derivatives thereof. Such other agents are illustrated with a substance having the mineral absorption promoting action and/or an enhancing action on cyclic tetrasaccharide and/or saccharide derivatives thereof having the mineral absorption promoting action: for example, saccharides such as isomaltooligosaccharides, galactooligosaccharides, fractooligosaccharides, nigerooligosaccharides, xylooligosaccharides, agarooligosaccharides, chitooligosaccharides, beet oligosaccharides, α,α-trehalose, saccharide derivatives of α,α-trehalose including α-glucosyl α,α-trehalose and α-maltosyl α,α-trehalose, lactosucrose, sorbitol, maltitol, lactitol, xylitol, erythritol and cyclic difractose; vitamins or derivatives thereof such as vitamin D, vitamin K including phylloquinone, menaquinone and menadione, and ascorbic acid; hormone preparations such as calcitonin preparation, estrogen preparation, protein anabolic hormone preparation and bisphosphonate; and polyphenols. Such polyphenols are illustrated with flavones, flavonols, flavanones, flavanonols, anthocyanidins, flavanols, chalcones, aurones, and their derivatives including precursors, aglycons and glycosides. These polyphenols or derivatives thereof can be further methylated ethylated, methoxylated, ethoxylated, sulfated or glycosylated. One or more members selected from the group consisting of the above-described substances can be used. Particularly, hesperetin, hesperidin, enzyme treated hesperidin, methylated hesperidin, naringenin, narindin, enzyme treated narindin, quercetin, rutin, enzyme treated rutin, eriodictin, eriodictyol, proanthocyanidin, catechin, epicatechin, epigallocatechin, tannin or hamamelitannnin is advantageously used in view of efficiently enhancing the mineral absorption promoting activity of cyclic tetrasaccharide and/or saccharide derivatives thereof. Minerals having the calcium absorption promoting action, such as zinc and magnesium, can be incorporated as agents having the mineral absorption-promoting action in the accelerator of the present invention.

The accelerator of the present invention can be applied for domestic animals such as a cow, horse and pig; domestic fowls such as a chicken and duck; cultured fishes or shellfishes such as a bream, flatfish, young yellowtail, short-neck clam and clam; cultured conchostracans such as a shrimp and crab; insects such as a silkworm and honeybee; and pets such as conchostracans, mammals including dogs and cats, birds, reptiles, amphibian, fishes and shellfishes as well as for humans.

The accelerator of the present invention containing cyclic tetrasaccharide and/or saccharide derivatives thereof as effective ingredients can be used alone, or if necessary, used by mixing with a filler, excipient or binder in order to be formed into various shapes such as a syrup, paste, masquite, powder, crystalline granule, sphere, short stick, plate, cube and tablet.

The accelerator of the present invention, containing cyclic tetrasaccharide and/or saccharide derivatives thereof, well harmonizes with other materials having other tastes such as acid taste, salty taste, astringent taste, delicious taste and bitter taste, and lowers the foreign taste and smell of the materials. Since it is highly acid-resistant and heat-resistant, it can be advantageously used as a raw material for general foods, beverages, quasi-drugs, pharmaceuticals and feeds. The products containing the accelerator of the present invention can be used in the same manner as in products without the accelerator, and they will be imparted with the mineral absorption promoting action and the calcium containing tissues including bones and teeth strengthening action. Therefore, they can be advantageously used as foods, beverages, quasi-drugs, pharmaceuticals, intermediate product thereof or raw materials thereof for treating or preventing bone disorders such as osteoporosis, bone fracture and backache; tooth disorders such as dental caries and periodontosis; urinary diseases such as nephrolithiasis; circulatory diseases such as hypertension and ischemic heart disease; anemia; diabetes; and reduction of homeostatic function. In addition, they can be used as an agent for strengthening bone, agent for strengthening calcium-containing tissues, or agent for reducing foreign taste and foreign smell. Further, they can be used for feeds or pet foods of domestic animals, domestic fowls and pets in the same manner.

The accelerator of the present invention is used for producing various foods and beverages such as seasonings, complex seasonings, Japanese confectioneries, Western confectioneries, breads, water ices, syrups, pastes, processed vegetable products, pickled vegetables, premixes for pickles vegetable, meat products, fish products, shellfish products, viands, side dish products, dairy products, soft drinks, premixes, instant foods, cold-stored foods, frozen foods, chilled foods, retort pouches, dried foods, baby foods, therapeutic diets, ampuled liquid medicines, peptide foods and frozen foods. Such foods and beverages, having the mineral absorption promoting ability and/or bone strengthening ability, can be advantageously used as a composition for promoting mineral absorption and/or strengthening bone. The accelerator, containing cyclic tetrasaccharide and/or saccharide derivatives thereof as effective ingredients, can be further contained in feeds or pet foods for breeding animals such as domestic animals, domestic fowls, honeybees, silkworms, freshwater fishes and conchostracan, in order to impart the mineral absorption promoting ability and/or calcium containing tissue strengthening ability.

Method for incorporating the accelerator of the present invention in a desired composition is not specifically restricted. The accelerator can be incorporated in a desired composition at any step during the process or in the final product. Such method can be selected from mixing, kneading, dissolving, melting, dispersing, suspending, emulsifying, soaking, crystallizing, dispersing, applying, attaching, spraying, coating, injecting, crystallizing and solidifying.

The accelerator of the present invention contains cyclic tetrasaccharide and/or saccharide derivatives thereof in a total amount of about 0.1% by weight or more (hereinafter, "% by weight" may be represented by "%"), preferably 0.5% or more, more preferably 1.0% or more. The accelerator can simply contain cyclic tetrasaccharide and/or saccharide derivatives thereof and optionally contain other saccharides deriving from the process of cyclic tetrasaccharide and/or saccharide derivatives thereof, such as glucose, isomaltose, maltose, oligosaccharides and dextrin, as long as it exerts the mineral absorption promoting action and/or bone strengthening action. While, the accelerator of the present invention, in the case of containing reducing saccharides such as glucose, may cause the deterioration of a composition which it contains as an effective ingredient a physiologically active substance having an amino group(s) intramolecularly, i.e., amino acids, by Maillard reaction. Therefore, the accelerator of the present invention preferably contains cyclic tetrasaccharide and/or saccharide derivatives thereof in an amount of 98% or more, desirably 99% or more, more desirably 99.5% or more. Optionally, it is subjected to hydrogenating reducing saccharides co-existing with cyclic tetrasaccharide and/or saccharide derivatives thereof to lower the reducing power. Since cyclic tetrasaccharide and/or saccharide derivatives thereof have a satisfactory stability, they may be used in combination with one or more members selected from the group consisting of reducing saccharides, non-reducing saccharides excluding cyclic tetrasaccharide and saccharide derivatives thereof, cyclodextrin, sugar alcohols, dietary fibers and water-soluble polysaccharides, sweeteners excluding above, spices, acidifiers, delicious taste imparting seasoning, liquors, organic acids, nonorganic acids, alkaline chemicals, emulsifiers, perfumeries, colorants, antioxidants and chelating substances in order to improve the dispersion property and increase the volume as long as the effect and quality of the composition is not reduced. If necessary, it may be used in combination with an appropriate amount of one or more members selected from the group consisting of preservatives, delicious taste imparting agents, sweeteners, stabilizers, alcohols and bactericides.

The accelerator of the present invention may be used in combination with an appropriate amount of one or more members selected from the group consisting of saccharides or sweeteners such as a powdery starch, glucose, maltose, sucrose, isomerized sugar, honey, maple sugar, dihydrochalcone, stevioside, α-glycosyl stevioside, rebaudioside, glycyrrhizin, L-aspartyl-L-phenylalanine methyl ester, saccharin, glycine, alanine, acesulfame-K and sucralose. It can be also admixed with a filler such as dextrin, starch and lactose.

The accelerator of the present invention is not restricted to a specific daily dose as long as it can exert the mineral absorption promoting action and/or bone strengthening action. The dose of cyclic tetrasaccharide and/or saccharide derivatives thereof is usually about 0.01 g/kg body weight per day or more, preferably about 0.5 g/kg body weight per day or more, more preferably about 1.0 g/kg body weight per day or more, on a dry solid basis. A daily dose less than 0.01 g/kg body weight may be insufficient to effectively exert the mineral absorption-promoting action. The accelerator can be administered at any frequency as long as it can exert the mineral absorption-promoting action and/or bone-strengthening action. It can be administered once a whole daily dose or at several times a day in a divisional manner. Usually, the latter is rather preferable because the accelerator might cause diarrhea in the case of administration in an excessive dose at once to people having a predisposition to diarrhea. Particularly, the accelerator is preferably used as a raw material for producing meal or taken before or after meal. The accelerator of the present invention can be orally administered alone or in a composition such as a food, beverage, pharmaceutical and quasi-drug. If such administrations are impossible, it can be directly injected into stomach or intestine though a catheter, etc.

The following experiments explain the accelerator for mineral absorption containing cyclic tetrasaccharide or a mixture containing cyclic tetrasaccharide and saccharide derivatives thereof in more detail.

Experiment 1

Influence of Taking Cyclic Tetrasaccharide on Mineral Absorption in Rats

As disclosed in the specification of International Publication No. WO01/090338, it is known that cyclic tetrasaccharide acts as a dietary fiber. The dietary fiber is known to inhibit mineral absorption and increase the excretion of minerals as disclosed, for example, in "Shokumotsu-Seni, Kiso-to-Rinsho (Dietary fiber, basic and clinical)", published by Asakura Publishing Company, Tokyo, Japan, 1997. Therefore, the following experiment was carried out in order to determine how cyclic tetrasaccharide influenced the mineral absorption.

Experiment 1-1

Breeding and Weighing Rats

Forty of Wister rats weighing 110 to 120 g (five-weeks aged male, commercialized by Charles River Japan Inc., Yokohama, Japan) were bred with a feed containing ingredients (%) shown in Table 1 for one week in order to be familiarized. The familiarized rats were randomly divided into four groups with ten rats each. Each group was experimentally bred for eight weeks with either a feed without cyclic tetrasaccharide shown in Table 1 (hereinafter, it is called as "basic feed"), or another feed of basic feed supplemented with 1%, 2% or 5% on a dry solid basis, of cyclic tetrasaccharide in a crystalline anhydrous powder form with a purity of 99.5%, prepared in the following Example A-3. These basic feed and three kinds of feeds with cyclic tetrasaccharide were prepared to contain 44.75% of the total amount of cyclic tetrasaccharide and corn starch in each feed. From one week before the end of the breeding test, in order to determine the metabolism of calcium, magnesium, iron, sodium, potassium and phosphorus (hereinafter, may be called "minerals" in all), rats in the all groups were fed with the four types of feeds supplemented with 0.5% of chromium oxide as a non-absorbed marker for the minerals. The rats were bred at 25° C. in a manner of freely allowing to take feeds and water under a condition of 12 hours regular interval between of light and shade. After completion of experimental breeding, all rats were individually weighed to calculate the average of weight and further calculate the rate of increased weight for each group. The result is shown in Table 2. In addition, Table 2 also shows the value of total amount of feed taken by one rat and the intake value average of cyclic tetrasaccharide per rat's weight a day.

TABLE 1

| Ingredient | Feed supplemented with no cyclic tetrasaccharide | Feed supplemented with 1% cyclic tetrasaccharide, on a dry solid basis | Feed supplemented with 2% cyclic tetrasaccharide, on a dry solid basis | Feed supplemented with 5% cyclic tetrasaccharide, on a dry solid basis |
|---|---|---|---|---|
| Cyclic tetrasaccharide | 0.0 | 1.0 | 2.0 | 5.0 |
| Corn starch | 39.75 | 38.75 | 37.75 | 34.75 |

TABLE 1-continued

| Ingredient | Feed supplemented with no cyclic tetrasaccharide | Feed supplemented with 1% cyclic tetrasaccharide, on a dry solid basis | Feed supplemented with 2% cyclic tetrasaccharide, on a dry solid basis | Feed supplemented with 5% cyclic tetrasaccharide, on a dry solid basis |
|---|---|---|---|---|
| α-Starch | 13.20 | 13.20 | 13.20 | 13.20 |
| Casein | 20.00 | 20.00 | 20.00 | 20.00 |
| Sucrose | 10.00 | 10.00 | 10.00 | 10.00 |
| Soybean oil | 7.00 | 7.00 | 7.00 | 7.00 |
| Cellulose | 5.0 | 5.0 | 5.0 | 5.0 |
| "Mineral Mix ™" | 3.50 | 3.50 | 3.50 | 3.50 |
| "Vitamin Mix ™" | 1.00 | 1.00 | 1.00 | 1.00 |
| D,L-Methionine | 0.30 | 0.30 | 0.30 | 0.30 |
| Choline bitartrate | 0.25 | 0.25 | 0.25 | 0.25 |
| t-Butyl hydroquinone | 0.0014 | 0.0014 | 0.0014 | 0.0014 |

TABLE 2

| Item | Base feed | Feed supplemented with 1% cyclic tetrsaccharide, on a dry solid basis | Feed supplemented with 2% cyclic tetrasaccharide, on a dry solid basis | Feed supplemented with 5% cyclic tetrasaccharide, on a dry solid basis |
|---|---|---|---|---|
| Weight (g/head) | 408 | 412 | 432 | 415 |
| Weight increased in the breeding test (g/rat/56 days) | 245 | 250 | 270 * | 253 |
| Total amount of intake of feed in the breeding test (g/rat/56 days) | 1166 | 1132 | 1227 * | 1200 |
| Intake value average of cyclic tetra-saccharide per kg body weight a day in the breeding test (g/rat/day) | 0 | 0.49 | 1.01 | 2.58 |

* Significantly difference level against base feed (p < 0.05)

Two days before the end of the breeding test, rats were placed into a gauge for measuring metabolism to collect their excrement in two days. The resulting excrement was subjected to the measurement of the contents of cyclic tetrasaccharide, each mineral, and chromium. After the breeding test, the rats were anatomized in an anesthetized condition to take out their alimentary canals including jejunum, intestinum ileum, appendix and colon/rectum. After the resulting alimentary canals were weighed, their contents were also weighed and subjected to the measurement of the amount of cyclic tetrasaccharide, minerals and chromium. The rats, which had been taken out their alimentary canals, were dislocated at their cervical vertebrae and taken out their femurs from right legs. The resulting femurs were subjected to the measurement of the amount of ashes, calcium, magnesium and phosphorus. The following(s) explain the methods of quantitative analysis of cyclic tetrasaccharide and the methods of measurement of minerals and chromium.

<Method of Quantification of Cyclic Tetrasaccharide>

One gram of a feed was admixed with 5 ml of 80% ethanol heated at 85° C. under reflux for 15 minutes to extract saccharides. The resulting saccharide sample was subjected to TMS derivatization in a usual manner. Three microliters of the sample was applied to a gas chromatography ("GC-16™", commercialized by Shimazu Corporation, Kyoto, Japan) equipped with OV-17 packed column ("2% Silicone, OV-17 Chromosorb W/AW DMSC 80-100 mesh, 3 mmID×2 m, SUS", produced by GL Science Corporation). The inner column temperature was kept at 160° C. for two minutes, and heated up to 320° C. at a rate of 7.5° C./min. The amount of cyclic tetrasaccharide was quantified by using nitrogen gas as a carrier (35 ml/min). While, in order to quantify the amounts of the contents of jejunum, intestinum ileum, appendix, colon/rectum and excrement, 0.05 g of each sample was weighed in a micro tube for gas chromatography and dried in a desiccator with phosphorus pentoxide. The resulting samples were subjected to TMS derivatization in a usual manner and quantified by gas chromatography.

<Method for Quantifying Calcium, Magnesium, Iron, Phosphorus and Chromium>

Two grams of a feed was preciously weighed in a porcelain crucible, heated to carbonize, and heated at 600° C. to incinerate. After weighed, the resulting test samples were admixed with hydrochloric acid in a precious analysis grade (concentration of 20%, commercialized by Wako Pure Chemicals, Co., Ltd., Osaka, Japan) to give a final concentration of 1%. They were subjected to atomic absorption spectrometry ("Zeeman5100™", commercialized by PerkinElmer); in the case of measurement of chromium, they were subjected to a flameless type one. In the case of measurement of phosphorus, they were subjected to usual molybdenum blue absorptiometry. On the other hand, 0.1 g of each of the contents of jejunum, intestinum ileum, appendix, colon/rectum, and excrement was subjected to wet-type incineration to prepare test samples similarly as in the above case of feed, and the test samples were quantified. The right femurs taken out from the anatomized rats were dried at 105° C. for 15 hours and measured as a dry weight. The resulting dried femurs were precisely weighed in a porcelain crucible, and incinerated similarly as in the case of the feed. The resultants were weighed and quantified for calcium, magnesium and phosphorus.

Table 3 shows the results of the measurements of the amount of cyclic tetrasaccharide in the feed, content of intestinum ileum, content of appendix, and excrement. Based on these results and the measurements of the amount of chromium in the feed, content of intestinum ileum, content of appendix and excrement shown in the following Table 5, the remaining percentages of cyclic tetrasaccharide in the content of intestinum ileum, content of appendix and excrement were calculated. The result is shown in Table 3. The remaining percentages (%) were calculated using the following numerical formula, based on the rate of the amount of cyclic tetrasaccharide to chromium in each feed and the rate of those in the contents or excrement in consideration of that chromium is never absorbed by living bodies;

Numerical Formula:

{(Amount of cyclic tetrasaccharide in each content or excrement/Amount of chromium in each content or excrement)/(Amount of cyclic tetrasaccharide in each feed/Amount of chromium in each feed)}×100

TABLE 3

| Amount of cyclic tetrasaccharide in feed (%) | Amount of cyclic tetrasaccharide in feed (mg/g) | Amount of cyclic tetrasaccharide in the content of alimentary canal or excrement (mg/g) (remaining percentage (%)) | | |
|---|---|---|---|---|
| | | Content of intestinum ileum | Content of appendix | Excrement |
| 1 | 8.9 | 60.5(95) | 0.0(0) | 0.0(0) |
| 2 | 18.7 | 184.1(95) | 0.0(0) | 0.0(0) |
| 5 | 44.2 | 298.0(90) | 0.0(0) | 0.0(0) |

As evident from the result shown in Table 3, in the rats bred with the feed supplemented with 1%, 2% or 5% of cyclic tetrasaccharide, at least 90% of cyclic tetrasaccharide was remained up to intestinum ileum without digestion but not detected at all in the appendix and excrement. While, the amount of organic acids including lactic acid was increased in supplemented depending on the amount of cyclic tetrasaccharide, and the pH reduction was observed. These results suggested that cyclic tetrasaccharide was digested by microorganisms in the appendix of rats.

The following Table 4 shows the result of measurement of the amount of mineral or chromium in the feeds. The following table 5 shows the result of the measurement of the amount of calcium, magnesium and chromium in the contents of intestinum ileum, appendix and colon/rectum or excrement. The following Table 6 shows the result for iron and phosphorus. Based on these results, the cumulative remaining rates in the contents of intestinum ileum, appendix and excrement, and the cumulative absorption rates to each alimentary canal were calculated. Tables 5 and 6 also show the results thereof. The absorbing rate (%) was calculated using the following numerical formula, based on the rate of the amount of each mineral to chromium in each feed and the rate of those in the contents or excrement, considering that chromium is never absorbed by living bodies;

Numerical Formula:

100−{[(Amount of each mineral in each content or excrement/Amount of chromium in each content or excrement)/(Amount of each mineral in each feed/Amount of chromium in each feed)]×100}

Further, Table 7 shows the result of the measurement of the dry weight, ash, calcium, magnesium and phosphorus of the femur.

TABLE 4

| Item | Base feed | Feed supplemented with 1% cyclic tetrasaccharide, on a dry solid basis | Feed supplemented with 2% cyclic tetrasaccharide, on a dry solid basis | Feed supplemented with 5% cyclic tetrasaccharide, on a dry solid basis |
|---|---|---|---|---|
| Amount of calcium (mg/g) | 3.87 | 4.10 | 3.32 | 4.30 |
| Amount of magnesium (mg/g) | 0.88 | 0.90 | 0.78 | 0.93 |
| Amount of phosphorus (mg/g) | 3.00 | 3.00 | 2.97 | 2.99 |
| Amount of iron (µg/g) | 33.8 | 41.3 | 35.2 | 45.7 |
| Amount of sodium (mg/g) | 4.31 | 3.85 | 3.53 | 4.84 |
| Amount of potassium (mg/g) | 4.49 | 5.19 | 3.78 | 4.40 |
| Amount of chromium (µg/g) | 10.89 | 9.91 | 8.81 | 10.39 |

TABLE 5

| | Item | Amount of calcium [mg/g] (Absorption percentage [%]) | Amount of magnesium [mg/g] (Absorption percentage [%]) | Amount of chromium [mg/g] |
|---|---|---|---|---|
| Intestinum ileum | Basic feed | 8.56 (75) | 1.93 (76) | 0.101 |
| | Feed supplemented with 1% cyclic tetra-saccharide | 6.02 * (79) | 1.30 * (80) | 0.070 |
| | Feed supplemented with 2% cyclic tetra-saccharide | 5.61 * (84) | 1.61 * (80) | 0.092 |

TABLE 5-continued

|  | Item | Amount of calcium [mg/g] (Absorption percentage [%]) | Amount of magnesium [mg/g] (Absorption percentage [%]) | Amount of chromium [mg/g] |
|---|---|---|---|---|
|  | Feed supplemented with 5% cyclic tetra-saccharide | 3.48 * (89) | 1.04 * (84) | 0.075 |
| Appendix | Basic feed | 11.48 (81) | 2.64 (81) | 0.173 |
|  | Feed supplemented with 1% cyclic tetra-saccharide | 10.56 * (83) | 2.24 * (84) | 0.153 |
|  | Feed supplemented with 2% cyclic tetra-saccharide | 8.98 * (88) | 2.40 * (86) | 0.201 |
|  | Feed supplemented with 5% cyclic tetra-saccharide | 4.99 * (93) | 2.03 * (88) | 0.192 |
| Colon/Rectum | Basic feed | 11.99 (84) | 2.81 (84) | 0.215 |
|  | Feed supplemented with 1% cyclic tetra-saccharide | 9.83 * (86) | 2.17 * (86) | 0.199 |
|  | Feed supplemented with 2% cyclic tetra-saccharide | 7.45 * (90) | 2.09 * (88) | 0.199 |
|  | Feed supplemented with 5% cyclic tetra-saccharide | 5.00 * (94) | 1.55 * (91) | 0.183 |
| Excrement | Basic feed | 60.43 (85) | 13.01 (86) | 1.202 |
|  | Feed supplemented with 1% cyclic tetra-saccharide | 54.29 * (88) | 12.06 * (88) | 1.105 |
|  | Feed supplemented with 2% cyclic tetra-saccharide | 28.62 * (92) | 9.21 * (90) | 1.042 |
|  | Feed supplemented with 5% cyclic tetra-saccharide | 26.47 * (94) | 8.37 * (93) | 1.400 |

* Significant difference level ($p < 0.05$) against basic feed.

TABLE 6

|  | Item | Amount of Phosphorus [mg/g] (Absorption percentage [%]) | Amount of iron [mg/g] (Absorption percentage [%]) |
|---|---|---|---|
| Intestinum ileum | Basic feed | 4.62 (83) | 0.11 (63) |
|  | Feed supplemented with 1% cyclic tetra-saccharide | 3.45 * (84) | 0.10 * (67) |
|  | Feed supplemented with 2% cyclic tetra-saccharide | 4.17 * (87) | 0.12 * (67) |
|  | Feed supplemented with 5% cyclic tetra-saccharide | 2.84 * (87) | 0.10 * (69) |
| Appendix | Basic feed | 5.82 (87) | 0.15 (71) |
|  | Feed supplemented with 1% cyclic tetra-saccharide | 5.39 * (88) | 0.16 * (74) |
|  | Feed supplemented with 2% cyclic tetra-saccharide | 5.35 * (92) | 0.18 * (77) |
|  | Feed supplemented with 5% cyclic tetra-saccharide | 3.43 * (93) | 0.19 * (78) |
| Colon/Rectum | Basic feed | 5.18 (91) | 0.15 (77) |
|  | Feed supplemented with 1% cyclic | 5.18 * (92) | 0.14 * (80) |

TABLE 6-continued

| Item | | Amount of Phosphorus [mg/g] (Absorption percentage [%]) | Amount of iron [mg/g] (Absorption percentage [%]) |
|---|---|---|---|
| | tetra-saccharide | | |
| | Feed supplemented with 2% cyclic tetra-saccharide | 4.10 * (94) | 0.14 * (83) |
| | Feed supplemented with 5% cyclic tetra-saccharide | 3.06 * (94) | 0.13 * (84) |
| Excrement | Basic feed | 20.45 (94) | 0.68 (81) |
| | Feed supplemented with 1% cyclic tetra-saccharide | 17.74 * (95) | 0.71 * (85) |
| | Feed supplemented with 2% cyclic tetra-saccharide | 10.27 * (97) | 0.49 * (88) |
| | Feed supplemented with 5% cyclic tetra-saccharide | 8.98 * (97) | 0.66 * (89) |

* Significant difference level ($p < 0.05$) against basic feed.

TABLE 7

| Item | Base feed | Feed supplemented with 1% cyclic tetrasaccharide on a dry solid basis | Feed supplemented with 2% cyclic tetrasaccharide on a dry solid basis | Feed supplemented with 5% cyclic tetrasaccharide on a dry solid basis |
|---|---|---|---|---|
| Dry weight (g) | 0.63 | 0.68 * | 0.71 * | 0.71 * |
| Amount of ash (g/g dry femur) | 0.63 | 0.64 * | 0.65 * | 0.66 * |
| Amount of calcium (mg/g dry femur) | 203 | 217 * | 225 * | 240 * |
| Amount of magnesium (mg/g dry femur) | 4.1 | 4.3 * | 4.4 * | 4.5 * |
| Amount of phosphorus (mg/g dry femur) | 108 | 115 * | 116 * | 118 * |

* Significant difference level ($p < 0.05$) against basic feed.

As evident from the results in Tables 5 and 6, the absorption rates of calcium, magnesium, phosphorus and iron in both intestinum ileum and lower alimentary canal than the intestinum canal were significantly increased in a dose-dependent manner of cyclic tetrasaccharide. As evident from the result in Table 7, the amounts of dried bone weight, ash, calcium, magnesium and phosphorus were significantly increased in comparing with the control in a dose-dependent manner of cyclic tetrasaccharide, respectively. While, there was no difference in dried bone weight between feeds containing 2% or 5% of cyclic tetrasaccharide. These results revealed that cyclic tetrasaccharide had the effect on promoting the absorption of calcium, magnesium, phosphorus and iron, further confirmed that it acted to increase the dried bone weight, the amount of ash, the amount of minerals and bone density, and to strengthen bone. Such effect of cyclic tetrasaccharide on promoting mineral absorption was found in intestinum ileum since the cyclic tetrasaccharide was hardly utilized therein. Therefore, the effect of cyclic tetrasaccharide on promoting mineral absorption was exerted by another mechanism different from the large intestine fermentation reported for maltitol, lactosucrose or fractooligosaccharide.

Experiment 2

Experiment 1 confirmed that cyclic tetrasaccharide promotes mineral absorption in alimentary canal of rat concretely in intestinum ileum or its upper alimentary canal. The following experiment was carried out in order to determine a part of alimentary canal, cyclic tetrasaccharide acts on to promote mineral absorption. Twenty heads of Wister rats (nine week aged male, commercialized by Charlesriver Corporation, Kanagawa, Japan) were bred for three days with a usual solid feed for rats. Under the anesthetization with ether, alimentary canal was taken out from each rat which had been bled from a jugular vein and treated by abdominal operation. Each alimentary canal was divided into jejunum, intestinum ileum and colon/rectum and washed with physiological saline to remove the content. The resulting jejunum specimen, intestinum ileum specimen or colon/rectum specimen was cut off to prepare each midsection sized with about 10 cm in length. The resulting midsection of each specimen was reversed using a glass rod and immersed in a physiological saline babbled with gas consisting of 95% oxygen and 5% carbon dioxide. The resultant was cut into pieces sized with 5 cm in length and each piece was tied with a suture thread at both ends to prepare a reversed canal sac, and injected with about 0.5 ml of an internal sac solution containing 30 mM Tris-HCl buffer (pH 7.4), 125 mM sodium chloride, 4 mM potassium chloride, 10 mM glucose and 1.25 mM calcium chloride (dihydrate) with a syringe and weighed. The resulting sac was immersed in an external sac solution (being bubbled with the gas consisting of 95% oxygen and 5% carbon dioxide) containing 50 mM, 100 mM or 200 mM of the same cyclic tetrasaccharide to Experiment 1 in the above solution containing 30 mM Tris-HCl buffer (pH 7.4), 125 mM sodium chloride, 4 mM potassium chloride, 10 mM glucose and 1.25 mM calcium chloride (dihydrate). At 15 or 30 minutes after the immersion, the reversed canal sac was taken out from the solution and washed with distilled water. The internal sac solution was collected from the resulting sac and admixed with distilled water to give a final volume of 25 ml. The resulting solution was subjected to a calorimetric measurement of calcium content using "CALCIUM TEST C WAKO™" (commercialized by Wako Pure Chemicals Corporation, Osaka, Japan). As a negative control, an external sac solution without saccharides. As a positive control, an external sac solution containing 200 mM maltitol, reported to have the effect on promoting mineral absorption though intestinal canal, instead of cyclic tetrasaccharide were prepared and carried out in the same manner. Speed of calcium absorption (nmol/min·cm$^2$) and its relative values defining the value of negative control as 100 were calculated. The result was shown in Table 8.

TABLE 8

| Saccharide added to external sac solution | Absorption speed of calcium in each alimentary canal sac ** (nmol/min · cm$^2$) | | |
|---|---|---|---|
| (Concentration) | Jejunum | Intestinum ileum | Colon/Rectum |
| Control (0 mM) | 21.4 (100) | 27.1 (100) | 13.3 (100) |
| Cyclic tetrasaccharide (50 mM) | 26.5 *✗ (124) | 33.6 *✗ (124) | 13.5 ✗ (101) |
| Cyclic tetrasaccharide (100 mM) | 37.6 *✗ (176) | 46.0 *✗ (167) | 14.6 *✗ (109) |
| Cyclic tetrasaccharide (200 mM) | 39.0 *✗ (183) | 52.9 *✗ (195) | 15.4 *✗ (116) |
| Maltitol (200 mM) | 27.9 * (131) | 40.5 * (150) | 22.3 * (168) |

* Significant difference level ($p < 0.05$) against control.
✗ Significant difference level ($p < 0.05$) against maltitol (excluding the control).
** Parenthetic value means the relative value when a control value is regarded as 100.

As evident from the result in Table 8, in the case of immersing the reversed sac prepared from jejunum, intestinum ileum and colon/rectum in the external sac solution, it showed a more active promotion of calcium absorption in a dose dependent manner than in the case of without saccharide. Cyclic tetrasaccharide strongly promoted the calcium absorption in jejunum and intestinum ileum but slightly in colon/rectum. While maltitol strongly promoted the calcium absorption in jejunum, intestinum ileum and colon/rectum. The result well corresponds to the result of Experiment 1 which shows that cyclic tetrasaccharide has an effect on promoting the mineral absorption in intestinum ileum. It is known that calcium is absorbed from alimentary canal; through active transport by an intracellular calcium transporter in jejunum and intestinum ileum, or through passive diffusion in colon/rectum. In addition, it is reported that maltitol is converted into organic acids by intestinal fermentation. As a result, unlike maltitol, cyclic tetrasaccharide is thought to promote the calcium absorption due to active transport through intracellular calcium transporters by acting on cells of upper alimentary canal such as jejunum and intestinum ileum. In considering the result of Experiment 1 where cyclic tetrasaccharide promotes the absorption of similarly as calcium, such as magnesium and phosphorus in the upper alimentary canal, it is concluded that cyclic tetrasaccharide has an effect on actively promoting mineral absorption in the upper alimentary canal such as jejunum and intestinum ileum.

The above experimental results reveal that a composition containing cyclic tetrasaccharide can be used for promoting mineral absorption and/or strengthening bone in living bodies.

The following Examples 1 to 8 concretely explain the accelerators of mineral absorption of the present invention, containing cyclic tetrasaccharide and/or saccharide derivatives thereof. The following Examples 9 to 29 concretely explain the compositions containing the accelerators. The present invention should not be restricted by these Examples.

Example 1

According to the method in Example 2 disclosed in the specification of International Publication No. WO 01/090338, an accelerator for mineral absorption in a syrup form had been prepared from potato starch. The accelerator had a concentration of 80% and contained 0.6% of glucose, 1.5% of isomaltose, 12.3% of maltose, 63.5% of cyclic tetrasaccharide, 5.2% of saccharide derivatives of cyclic tetrasaccharide formed in a manner of binding one or more glucose residues to the cyclic tetrasaccharide, and 16.9% of other saccharides, on a dry solid basis. The accelerator is used alone for promoting mineral absorption and/or strengthening bone, or optionally used for producing various compositions such as foods, beverages, quasi-drugs, pharmaceuticals and feeds for promoting mineral absorption by incorporating into raw materials including edible materials, pharmaceutical materials or feed materials, or intermediate products.

Example 2

According to the method in Example 9 disclosed in the specification of International Publication No. WO 01/090338 (except for omitting α-glucosidase and glucoamylase), an accelerator for mineral absorption in a syrup form had been prepared from cornstarch. The accelerator had a concentration of 73% and contained 4.1% of glucose, 8.1% of disaccharides including maltose or isomaltose, 4.6% of trisaccharides including maltotriose, 35.2% of cyclic tetrasaccharide, 15.6% of saccharide derivatives of cyclic tetrasaccharide which had structures binding one or more glucose residues to cyclic tetrasaccharide, and 32.4% of other saccharides, on a dry solid basis. The accelerator is used alone for promoting mineral absorption and/or strengthening bone, or optionally used for producing various compositions such as foods, beverages, quasi-drugs, pharmaceuticals and feeds by incorporating into raw materials including edible materials, pharmaceutical materials or feed materials, or intermediate products.

Example 3

A syrup containing cyclic tetrasaccharide prepared from corn starch according to the method in Example 4 disclosed in the specification of the International Publication No. WO 01/090338 was subjected to purifying, concentrating, drying, and crystallizing according to the methods in Examples 6 and 7 disclosed in the specification of the International Publication No. WO 01/090338 to produce an accelerator for mineral absorption in a powder form, which essentially consists of crystalline pentahydrous cyclic tetrasaccharide with a purity of 99.6%. The accelerator is used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products.

The crystalline pentahydrous cyclic tetrasaccharide was dried according to the method in Experiment 31 or 32 disclosed in the specification of the International Publication No. WO 01/090338 to produce accelerators for promoting mineral absorption consisting of a powder containing of crystalline monohydrous cyclic tetrasaccharide or crystalline anhydrous cyclic tetrasaccharide. These accelerators are used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products.

Example 4

Sixty parts by weight of crystalline pentahydrous cyclic tetrasaccharide, prepared in Example 3, were admixed with 40 parts by weight of a commercialized crystalline anhydrous maltitol ("MABIT™", commercialized by Hayashibara Shoji Co., Ltd., Okayama, Japan) to produce an accelerator for mineral absorption in a powder form. The accelerator is used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products.

Example 5

Fifty parts by weight of crystalline pentahydrous cyclic tetrasaccharide, prepared in Example 3, were admixed with 50 parts by weight of a commercialized α,α-trehalose ("TREHA®", commercialized by Hayashibara Shoji Co., Ltd., Okayama, Japan) to produce an accelerator for mineral absorption in a powder form. The accelerator is used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products. In addition, the accelerator can be granulized or tableted by optionally adding sugar esters to be easily formed into a granule or tablet.

Example 6

A commercialized food grade crystalline hydrous α,α-trehalose ("TREHA®", commercialized by Hayashibara Shoji, Inc., Okayama, Japan) was dissolved in water and concentrated in vacuo by heating at 60° C. to give a trehalose solution with a concentration of 75%. The resulting solution was kept at ambient temperature to form crystal. The resulting crystal was washed with water twice, dried and pulverized to produce a crystalline hydrous α,α-trehalose powder with a purity of 99.8%. Fifty parts by weight of the resulting powder and fifty parts by weight of crystalline pentahydrous cyclic tetrasaccharide, prepared in Example 3, were admixed homogeneously to produce an accelerator for mineral absorption in a powder form. The accelerator is used alone for promoting mineral absorption and/or strengthening bone or optionally used for producing various compositions such as foods, beverages, quasi-drugs, pharmaceuticals and feeds by incorporating the product into raw materials including edible materials, pharmaceutical materials or feed materials, or intermediate products. Since the accelerator consists of cyclic tetrasaccharide and trehalose with a high purity, it is stable due to an extremely low reactivity. Therefore, it is advantageously used for easily-deteriorated compositions having an amino group(s) causing of Mailard reaction with reducing saccharides. In addition, the accelerator can be granulized or tableted by optionally adding sugar esters to be easily formed into a granule or tablet.

Example 7

Seventy parts by weight of the syrup containing cyclic tetrasaccharide and saccharide derivatives thereof, prepared in Example 1, were admixed with two parts by weight of ascorbic acid, one part by weight of vitamin $E_1$ and 0.5 part by weight of glycerin fatty acid ester to produce an accelerator for mineral absorption in a syrup form. The accelerator is used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products.

Example 8

Seventy parts by weight of crystalline pentahydrous cyclic tetrasaccharide, prepared in Example 3, were admixed with two parts by weight of ascorbic acid 2-glucoside (commercialized by Hayashibara Biochemical Laboratories, Inc., Okayama, Japan) and two parts by weight of enzyme-treated hesperidin ("αG HESPERIDIN™", commercialized by Toyo Sugar Refining, Co., Ltd., Tokyo, Japan) to produce a powdery mixture. The product is used alone for promoting mineral absorption and/or strengthening bone, or optionally used for producing various compositions such as foods, beverages, quasi-drugs, pharmaceuticals and feeds by incorporating the product into raw materials including edible materials, pharmaceutical materials or feed materials, or intermediate products.

Example 9

Table Sugar for Promoting Mineral Absorption

Fifty parts by weight of the accelerator for mineral absorption in a powder form containing crystalline pentahydrous cyclic tetrasaccharide, prepared by the method in Example 3, 46 parts by weight of crystalline anhydrous maltitol, three parts by weight of a glycosyl transferred hesperidin ("αG HESPERIDIN™", commercialized by Toyo Sugar Refining, Co., Ltd., Tokyo, Japan) and one part by weight of sucralose (commercialized by San-Ei Gen F.F.I. Inc., Osaka, Japan) were dissolved in 200 parts by weight of water and spray-dried in a usual manner to produce a powdery sweetener for promoting mineral absorption. The product, containing cyclic tetrasaccharide and glycosyl-transferred hesperidin, promotes the absorption of minerals taken from other foods and beverages.

Example 10

Sweetener for Promoting Mineral Absorption

Five parts by weight of the accelerator in a powder form containing crystalline monohydrous cyclic tetrasaccharide, prepared in Example 3, 94.5 parts by weight of a crystalline anhydrous maltitol powder ("MABIT®", commercialized by Hayashibara Shoji, Inc.) and 0.5 part by weight of an L-aspartyl-L-phenylalanine methyl ester ("ASPARTAME™", commercialized by Ajinomoto Co., Ltd., Tokyo, Japan) were mixed homogeneously and granulated in a usual manner to produce a granular sweetener for promoting mineral absorption. Since cyclic tetrasaccharide promotes the intestinal absorption of minerals taken from other foods and beverages, the product is used for strengthening bone of humans on a low-mineral diet. In addition, it is preferably used as a sweetener for preventing or treating lifestyle related diseases caused by lack of minerals such as osteoporosis and metabolism disorder. It also preferably used as a sweetness-imparting agent for pharmaceuticals.

Example 11

Powdery Oil for Promoting Mineral Absorption

One hundred parts by weight of soybean salad oil and one part by weight of lecithin were admixed with 10 parts by weight of water in ambient temperature. The resulting mixture was admixed with 100 parts by weight of the accelerator in a powder form, prepared in Example 5, powdered and sieved to produce a powdery oil for promoting mineral absorption. Since the product, containing cyclic tetrasaccharide, promotes the intestinal absorption of minerals taken from other foods and beverages when taken with foods, beverages or feeds produced by using the product, it is used for strengthening bone of humans on a low-mineral diet. In addition, it is preferably used for preventing or treating lifestyle related diseases caused by lack of minerals such as osteoporosis and metabolism disorder. Further, the product is advantageously used as a raw material for feed or pet food for animals requiring mineral supplements.

Example 12

Vegetable Juice for Promoting Mineral Absorption 97.5 parts by weight of a commercialized vegetable juice were admixed with one part by weight of xyloglucan hydrolysate, one part by weight of the accelerator in a syrup form, prepared in Example 2, and 0.5 part by weight of glycosyl transferred naringin to produce a vegetable juice for promoting mineral absorption. Since cyclic tetrasaccharide promotes absorption of minerals taken from the product or other foods and beverages, the product is used for strengthening bones of humans on a low-mineral diet when the product, or food, beverage or feed made of thereof is taken. Further, it is advantageously used for treating or preventing diseases including lifestyle-related diseases caused by lack of minerals such as osteoporosis and metabolic disorders, and as a feed or pet food for animals requiring mineral supplements. In addition, the product is lowered in bitter taste characteristic to vegetable and is a delicious vegetable juice.

Example 13

Beer for Promoting Mineral Absorption

One hundred parts by weight of a fermentative solution attached by a commercialized beer preparation kit ("NB Beer Basic Set™", commercialized by Tokyu Hands Inc., Tokyo, Japan) were admixed with two parts by weight of the accelerator in a syrup form, prepared by the method in Example 1, to produce a beer according to the attached manual. Since the product promotes absorption of minerals taken from the product or other foods and beverages when it is taken, it is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements. In addition, the product is lowered in unpleasant taste and/or unpleasant smell characteristic to beer and is a sharp and delicious beer.

Example 14

Powdery Ginseng Extract for Promoting Mineral Absorption

One part by weight of five-fold concentrated ginseng extract was admixed with two parts by weight of crystalline hydrous trehalose and four parts by weight of the accelerator in a syrup form, prepared in Example 1, and dissolved by stirring. The resulting solution was spray-dried in a usual manner to produce a powdery ginseng extract for promoting mineral absorption. Since the product contains cyclic tetrasaccharide and saccharide derivatives thereof, when the product, or a food, beverage or feed made thereof is taken, the product promotes absorption of minerals taken from the product or other foods and beverages. Therefore, it is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements. In addition, the product is lowered in bitter taste characteristic to ginseng extract and is a delicious powdery ginseng extract.

Example 15

Powdery Royal Jelly for Promoting Mineral Absorption

One part by weight of frozen raw royal jelly was admixed with 0.2 part by weight of powdery propolis and nine parts by weight of the mixture containing crystalline monohydrous cyclic tetrasaccharide and the same amount of crystalline anhydrous cyclic tetrasaccharide, pulverized in a usual manner to produce a powdery raw royal jelly for promoting mineral absorption. Since cyclic tetrasaccharide and royal jelly promote absorption of minerals taken from other foods and beverages, the product is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements. In addition, the product is lowered in smell characteristic to royal jelly and is an easily-taken powdery royal jelly.

Example 16

Chocolate Cookie for Promoting Mineral Absorption

A chocolate cookie for promoting mineral absorption was produced in a usual manner using 140 parts by weight of wheat flour (weak flour), 90 parts by weight of butter, 115 parts by weight of chocolate, 360 parts by weight of sugar, 200 parts by weigh of whole egg, 200 parts by weight of almond, 50 parts by weight of the accelerator in a powder form containing crystalline monohydrous cyclic tetrasaccharide, prepared by the method in Example 3, and two parts by weight of coral calcium. Since cyclic tetrasaccharide promotes absorption of minerals taken from other foods and beverages, the product is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements. In addition, the product is lowered in characteristic and stuffy smell due to 2,3-butanedion from a heated chocolate and a delicious chocolate.

Example 17

Jelly for Promoting Mineral Absorption

Two hundreds parts by weight of framboise puree, 46 parts by weight of granulated sugar, 12 parts by weight of the accelerator in a syrup form, prepared in Example 2, 50 parts by weight of starch syrup, 122 parts by weight of α,α-trehalose ("TREHA®", commercialized by Hayashibara Shoji, Inc., Okayama, Japan), five parts by weight of pectin, three parts by weight of 50% citric acid aqueous solution, 27 parts by weight of isomerized sugar, and appropriate amount of water were mixed together, dissolved and boiled down slowly to about Brix 78. The resultant was poured in an appropriate mold and cooled at ambient temperature to produce a hard jelly for promoting mineral absorption. Since cyclic tetrasaccharide and saccharide derivatives thereof promote absorption of minerals taken from other foods and beverages, the product is used for strengthening bones of humans on a low-mineral diet. Further, the product is advantageously used for treating or preventing diseases including lifestyle-related diseases caused by lack of minerals such as osteoporosis and metabolic disorders.

Example 18

Hard Candy for Promoting Mineral Absorption

Sixty parts by weight of sugar, 20 parts by weight of α,α-trehalose ("TREHA®", commercialized by Hayashibara Shoji, Inc., Okayama, Japan), 35 parts by weight of the accelerator in a syrup form, prepared by the method in Example 1, 1.5 parts by weight of a mixture of amino acids, and 85 parts by weight of water were mixed together to produce a hard candy for promoting mineral absorption in a usual manner. Since cyclic tetrasaccharide and saccharide derivatives thereof promote absorption of minerals taken from other foods and beverages, the product is used for strengthening bones of humans on a low-mineral diet. Further, the product is advantageously used for treating or preventing diseases including lifestyle-related diseases caused by lack of minerals such as osteoporosis and metabolic disorders.

Example 19

Rice Flour Bread for Promoting Mineral Absorption

Four hundreds parts by weight of a rice flour containing gluten for bread ("KOME NO KO (for bread)™", commercialized by Saitoh Flour Milling Inc., Niigata, Japan), eight parts by weight of sodium chloride, 40 parts by weight of the accelerator containing crystalline pentahydrous cyclic tetrasaccharide as an effective ingredient in a powder form, prepared in Example 3, 12 parts by weight of white superior soft sugar, 12 parts by weight of skim milk, one part by weight of raw yeast, eight parts by weight of pullulan, 320 parts by weight of water were mixed together by stirring with a vertical mixer, further admixed with 20 parts by weight of butter, and kneaded to prepare a dough. The resulting dough was kept at 25° C. for 50 minutes to ferment and cut into pieces in an appropriate size. The resultant was kept at RH75 and 35° C. for 50 minutes and baked in an oven controlled at the upper and lower temperature of 180° C. for 40 minutes to produce rice flour bread for promoting mineral absorption. Since the product contains cyclic tetrasaccharide, when the product is taken, it promotes the absorption of minerals taken from the product or other foods and beverages. Therefore, it is used for strengthening bones of humans on a low-mineral diet. Further, the product is advantageously used for treating or preventing diseases including lifestyle-related diseases caused by lack of minerals such as osteoporosis and metabolic disorders. In addition, the product is lowered in fermenting smell characteristic to yeast and is a delicious rice flour bread.

Example 20

Boiled Rice for Promoting Mineral Absorption

Three hundreds parts by weight of a washed and drained rice were immersed in an aqueous solution containing 375 parts by weight of water and 13.5 parts by weight of the accelerator in a powder form, prepared in Example 4, for one hour, and boiled with a rice cooker for family use to produce a boiled rice for promoting mineral absorption. Since the product contains cyclic tetrasaccharide, when the product is taken, it promotes the absorption of minerals taken from the product or other foods and beverages. Therefore, it is used alone or as a raw material for strengthening bones of humans on a low-mineral diet, and as a feed or pet food for animals requiring mineral supplements. In addition, the product is lowered in smell of rice bran and is a delicious boiled rice.

Example 21

Fishpaste Product for Promoting Mineral Absorption

Two thousands parts by weight of walleye pollack fresh meat immersed in water were admixed with 105 parts by weight of the accelerator in a powder form, prepared in Example 5, three parts by weight of sodium lactate and 0.2 part by weight of proanthocyanidin to produce a fishpaste. The fishpaste was frozen at −20° C. to produce a frozen fishpaste. After preserved at −20° C. for 90 days, the fishpaste was thawed, admixed with 100 parts by weight of a solution containing 150 parts by weight of iced water, 40 parts by weight of sodium glutamate, 100 parts by weight of potato starch, three parts by weight of sodium polyphosphate, 50 parts by weight of sodium chloride and five parts by weight of sorbitol, and minced. The resultant was molded by about 120 g and placed on a board. The resultant was steamed for 30 minutes to give an inner temperature of about 80° C. After cooled in ambient temperature, the resultant was kept at 4° C. for 24 hours to produce a fish paste product for promoting mineral absorption. Since cyclic tetrasaccharide and proanthocyanidin promote absorption of minerals, the product is used for diet or preventing lifestyle-related diseases. Further, it is advantageously used as a food or a material thereof for patients on a low-lipid diet, for example, patients with lifestyle-related diseases such as adiposis and hyperlipemia. The product is lowered in foreign smell due to the oxidation or decomposition and a delicious fishpaste product.

Example 22

Bacon for Promoting Mineral Absorption

Twenty-two parts by weight of sodium chloride, four parts by weight of the accelerator containing crystalline pentahydrous cyclic tetrasaccharide, prepared in Example 3, one part by weight of sugar, two parts by weight of sodium lactate, 2.0 parts by weight of sodium polyphosphate, 0.5 part by weight of ascorbic acid, 0.2 part by weight of sodium nitrite, and 68.8 parts by weight of water were mixed together and dissolved to prepare a pickle solution. One part by weight of the pickle solution was so slowly injected into nine parts by weight of pork spareribs as to be penetrated uniformly. The resultant was smoked in a usual manner to produce bacon for promoting mineral absorption. After smoked, it was left in an ambient temperature overnight, and sliced. The sliced bacon was vacuumized and preserved at 10° C. Since cyclic tetrasaccharide promotes the absorption of minerals taken from the product or other foods and beverages, the product is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements.

Example 23

Beverage Containing Mineral

Twenty-five parts by weight of sugar, five parts by weight of lactosucrose, 4.64 parts by weight of xanthane gum, 4.0 parts by weight of locust bean gum, 3.4 parts by weight of taragum, 1.7 parts by weight of psyllium seed gum, 1.2 parts by weight of ascorbic acid, 1.2 parts by weight of sodium chloride, 1.2 parts by weight of citric acid (crystalline), 0.12 part by weight of sodium citrate, 0.12 part by weight of potassium chloride, 0.5 part by weight of calcium lactate, 0.03 part by weight of magnesium sulfate, 0.05 part by weight of sucralose, perfumery, and 50 parts by weight of the accelerator, prepared in Example 2, were mixed together homogeneously. Eight parts by weight of the resulting mixture were dissolved in 92 parts by weight of water to produce a mineral drink in a gel form. Since cyclic tetrasaccharide and lactosucrose promote the absorption of minerals taken from the product or other foods and beverages, the product is advantageously used for efficiently supplementing minerals and moisture during sporting. Since the product is a gel form without concerning to enter the trachea differing from the case of water, it is also advantageously used for supplementing moisture and minerals against patients with dysphagia, aged people and children. In addition, the product is lowered in bitter taste of minerals and aftertaste of sucrose and sucralose, and is a flavorful beverage with its improved preference.

Example 24

Bittern

One hundred and forty-four parts by weight of the accelerator in a syrup form, prepared in Example 2, and 202 parts by weight of a commercialized bittern (produced by Sanuki Salt Manufacturing Co., Ltd., Kagawa, Japan) were mixed together and completely dissolved by heating at 70° C. The resultant was concentrated in vacuo to produce a solution having a solid content of 63%. Since cyclic tetrasaccharide promotes the absorption of minerals taken from the product or other foods and beverages, it is advantageously used as a raw material for sport drink, health food, or food for aged people or patients. It can be used as a solidifier for soybean curd, other foods and beverages, cosmetics, quasi-drugs, pharmaceuticals or feeds.

Example 25

Multivitamin Preparation

Five parts by weight of retinol palmitate, five parts by weight of ergocalciferol, 10 parts by weight of fursultiamine hydrochloride, five parts by weight of riboflavin, 10 parts by weight of pyridoxine chloride, 60 parts by weight of ascorbic acid, 10 parts by weight of tocopherol acetate, 30 parts by weight of nicotinamide, 0.01 part by weight of cyanocobalamin, and 40 parts be weight of calcium pantothenate were mixed by stirring. One part by weight of the resulting mixture was admixed with 24 parts by weight of the accelerator in a powder form, prepared in Example A-5, by stirring, and tableted by a tablet machine to produce a multivitamin preparation. Since cyclic tetrasaccharide promotes absorption of minerals taken from the product or other foods and beverages, the product with lowered in drug smell characteristic to vitamins is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements. In addition, the product is lowered in unpleasant taste and/or unpleasant smell including drug smell characteristic to vitamins and inhibited in the oxidation or decomposition, and an easily-eatable vitamin preparation without hygroscopicity even after preserved in a long period.

Example 26

Tablet for Promoting Mineral Absorption

Two hundreds parts by weight of γ-oryzanol, 650 parts by weight of the accelerator containing crystalline pentahydrous cyclic tetrasaccharide, prepared by the method in Example 3, 50 parts by weight of glycosyl-transferred hesperidin, four parts by weight of calcium carbonate, and two parts by weight of magnesium stearate were mixed together, and tableted in a usual manner to produce a tablet containing 250 mg per tablet. Since cyclic tetrasaccharide and glycosyl-transferred hesperidin promote the absorption of minerals taken from the product or other foods and beverages to strengthen calcium-containing tissues, the product is used for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements.

Example 27

Tablet Containing Minerals

Seventy-five parts by weight of precipitated calcium carbonate, three parts by weight of ferrous fumarate, 12 parts by weight of magnesium carbonate, three parts by weight of tocopherol acetate, five parts by weight of ascorbic acid, 200 parts by weight of the accelerator containing crystalline pentahydrous cyclic tetrasaccharide, prepared by the method in Example 3, one part by weight of sugar ester, were mixed homogeneously and tableted in a usual manner to produce a tablet containing 250 mg per tablet. Since cyclic tetrasaccharide promotes the absorption of minerals taken from the product or other foods and beverages to strengthen calcium-containing tissues, the product with a lowered bitter taste of minerals is used for strengthening bones of humans on a low-mineral diet. Further, the product is advantageously used for treating or preventing diseases including lifestyle-related diseases caused by lack of minerals such as osteoporosis and metabolic disorders, and as a feed or pet food for animals requiring mineral supplements.

Example 28

Mineral Preparation

Seventy-five parts by weight of precipitated calcium carbonate, three parts by weight of ferrous fumarate, 12 parts by weight of magnesium carbonate, 0.2 part by weight of zinc acetate, 0.01 part by weight of manganese carbonate, 0.001 part by weight of sodium selenate, five parts by weight of ascorbic acid 2-glucoside, one part by weight of glycosyl-transferred rutin, 200 parts by weight of the accelerator containing crystalline pentahydrous cyclic tetrasaccharide, prepared in Example 3, were mixed homogeneously to produce a mineral preparation. Since cyclic tetrasaccharide promotes the absorption of minerals taken from the product or other foods and beverages to strengthen calcium-containing tissues, the product with lowered foreign taste and smell including bitter taste, metal taste and metal smell of minerals including calcium, iron and magnesium is used alone or optionally after tableted for strengthening bones of humans on a low-mineral diet. Further, the product is advantageously used alone or as a raw material for treating or preventing diseases including lifestyle-related diseases caused by lack of minerals such as osteoporosis and metabolic disorders, and as a feed or pet food for animals requiring mineral supplements.

Example 29

Drink Supplemented with Vitamins and Minerals 0.15 part by weight of a mixture containing 10 parts by weight of thiamine nitrate, five parts by weight of riboflavin, 10 parts by weight of pyridoxine hydrochloride, 55 parts by weight of ascorbic acid 2-glucoside (produced by Hayashibara Biochemical Laboratories, Inc., Okayama, Japan), 30 parts by weight of nicotinamide, 0.01 part by weight of cyanocobalamin and 40 parts by weight of calcium pantothenate, one part by weight of aminoethylsulfonic acid, 0.1 part by weight of a commercialized bittern (produced by Sanuki Salt Manufacturing Co., Ltd., Kagawa, Japan), 0.01 part by weight of acesulfame-K, and five parts by weight of the accelerator containing crystalline pentahydrous cyclic tetrasaccharide, prepared by the method in Example 3, were dissolved in 93.7 parts by weight of purified water by stirring to produce a beverage supplemented with vitamins and minerals. Since cyclic tetrasaccharide promotes the absorption of minerals taken from the product or other foods and beverages, the product with lowered bitter tastes and drug smells is used for strengthening bones of humans on a low-mineral diet. Further, it is advantageously used for treating or preventing diseases including lifestyle-related diseases caused by lack of minerals such as osteoporosis and metabolic disorders, and as a feed or pet food for animals requiring mineral supplements.

Example 30

Mixed Feed for Promoting Mineral-Absorption

Thirty parts by weight of wheat bran, 35 parts by weight of skim milk, 10 parts by weight of rice bran, 10 parts by weight of a powder abundantly containing lactosucrose, 10 parts by weight of multivitamin, five parts by weight of fish meal, five parts by weight of dicalcium phosphate, three parts by weight of calcium carbonate, three parts by weight of oil, two parts by weight of magnesium acetate, one part by weight of glycosyl-transferred rutin, two parts by weight of sodium chloride, 0.001 part by weight of cobalt sulfate, 0.001 part by weight of ammonium molybdate, and five parts by weight of the accelerator in a syrup form, prepared by the method in Example 2, were mixed together to produce a mixed feed for promoting mineral absorption. Since cyclic tetrasaccharide, saccharide derivatives thereof and glycosyl-transferred rutin promote the absorption of minerals taken from the product or other foods and beverages, the product is preferably used as a feed for animals such as domestic animals, domestic fowls and pets, requiring mineral supplements, particularly, it is useful as a feed for a piglet.

INDUSTRIAL APPLICABILITY

The present invention relates to an accelerator for mineral absorption, containing cyclic tetrasaccharide composed of glucose as a constituent saccharide and/or saccharide derivatives thereof as an effective ingredient, and a composition containing the accelerator for promoting mineral absorption, which are used for promoting mineral absorption in animals including humans. Further, since these cyclic tetrasaccharide and/or saccharide derivatives thereof are safely taken orally and have a satisfactory stability, the accelerator containing such cyclic tetrasaccharide and/or saccharide derivatives thereof as effective ingredients can be used in various fields such as foods, beverages, cosmetics, quasi-drugs and pharmaceuticals. The present invention with such an outstanding function and effect is a significant invention that will greatly contribute to this art.

What is claimed is:
1. A method of treating a condition of osteoporosis or bone fracture, which comprises
administering an effective amount therefor of cyclic tetrasaccharide represented by cyclo {→6)-α-D-glucopyranosyl-(1→3)-α-D-glucopyranosyl-(1→6)-α-D-glu- copyranosyl-(1→3)-α-D-glucopyranosyl-(1→} and/or a saccharide derivative thereof
together with a calcium compound,
said saccharide derivative being a member selected from the group consisting of saccharides (I) where one or more of the same or different glycosyl residues are bound to said cyclic tetrasaccharide; saccharides (II) where one or more of the same or different glycosyl residues selected from the group consisting of α-D-glucopyranosyl residue, β-D-galactopyranosyl residue, and β-D-chitosaminyl residue have been transferred to one or more hydroxyl groups of the saccharides (I); and saccharides (III) where one or more of the same or different glycolyl residues selected from the group consisting of α-D-glucopyranosyl residue, β-D-galactopyranosyl residue, and β-D-chitosaminyl residue have been transferred to the α-D-glucopyranosyl residue, β-D-galactopyranosyl residue, and β-D-chitosaminyl residue of said saccharides (II),
wherein and whereby the mineral absorption of said calcium compound is accelerated.

2. The method of claim 1, wherein one or more members selected from the group consisting of casein phosphopeptide, vitamins, polyphenol, monosaccharides, oligosaccharides, water-soluble polysaccharides, sugar alcohols, cyclodextrins, spices, acidifiers, seasonings, liquors, organic acids, non-organic acids, emulsifiers, perfumeries and colorants is further administered.

3. The method of claim 2, wherein said vitamin is one or more members selected from the group consisting of vitamin D, vitamin K, L-ascorbic acid, and derivatives thereof.

4. The method of claim 2, wherein said polyphenol is one or more members selected from the group consisting of flavonoids, catechin and epigallocatechin.

5. The method of claim 2, wherein said oligosaccharide is one or more members selected from the group consisting of fractooligosaccharide, isomaltooligosaccharide, xylooligosaccharide, lactosucrose, soybean oligosaccharide, kojioligosaccharide, galactosylglucoside, saccharide derivative of α,α-trehalose, α,α-trehalose and/or α,β-trehalose.

6. The method of claim 1, wherein said cyclic tetrasaccharide and/or said saccharide derivative is administered at least at a dose of 0.01 g/kg body weight per day or more, on a dry solid basis.

7. The method of claim 1, comprising
administering the cyclic tetrasaccharide and the calcium to a person who has been diagnosed as suffering from a said condition.

* * * * *